US00PP36406P2

(12) United States Plant Patent
Hartman

(10) Patent No.: US PP36,406 P2
(45) Date of Patent: Jan. 21, 2025

(54) ***CALADIUM* PLANT NAMED 'RSB OF15-200'**

(50) Latin Name: ***Caladium* X *hortulanum***
Varietal Denomination: RSB OF15-200

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 0 days.

(21) Appl. No.: 18/657,766

(22) Filed: May 7, 2024

(51) Int. Cl.
*A01H 5/12* (2018.01)
*A01H 6/10* (2018.01)

(52) U.S. Cl.
USPC ..... Plt./373

(58) Field of Classification Search
USPC ..... Plt./373, 263.1
CPC ..... A01H 5/12; A01H 5/00; A01H 6/10
See application file for complete search history.

(56) References Cited

U.S. PATENT DOCUMENTS

PP27,093 P2 * 8/2016 Hartman ..... A01H 5/02 Plt./373

* cited by examiner

*Primary Examiner* — June Hwu
(74) *Attorney, Agent, or Firm* — C. Anne Whealy

(57) ABSTRACT

A new and distinct cultivar of *Caladium* plant named 'RSB OF15-200', characterized by its upright plant habit and intermediate to tall in height; moderately dense, leafy and bushy appearance; moderately vigorous growth habit and rapid growth rate; fancy-type leaves with centers that have variable hues of reddish pink and surrounded by dark green-colored marginal areas, entire leaf with variable and random greenish white-colored speckles; and petioles that are tannish green to tannish pink in color with greenish brown-colored stripes.

4 Drawing Sheets

Figure 1:
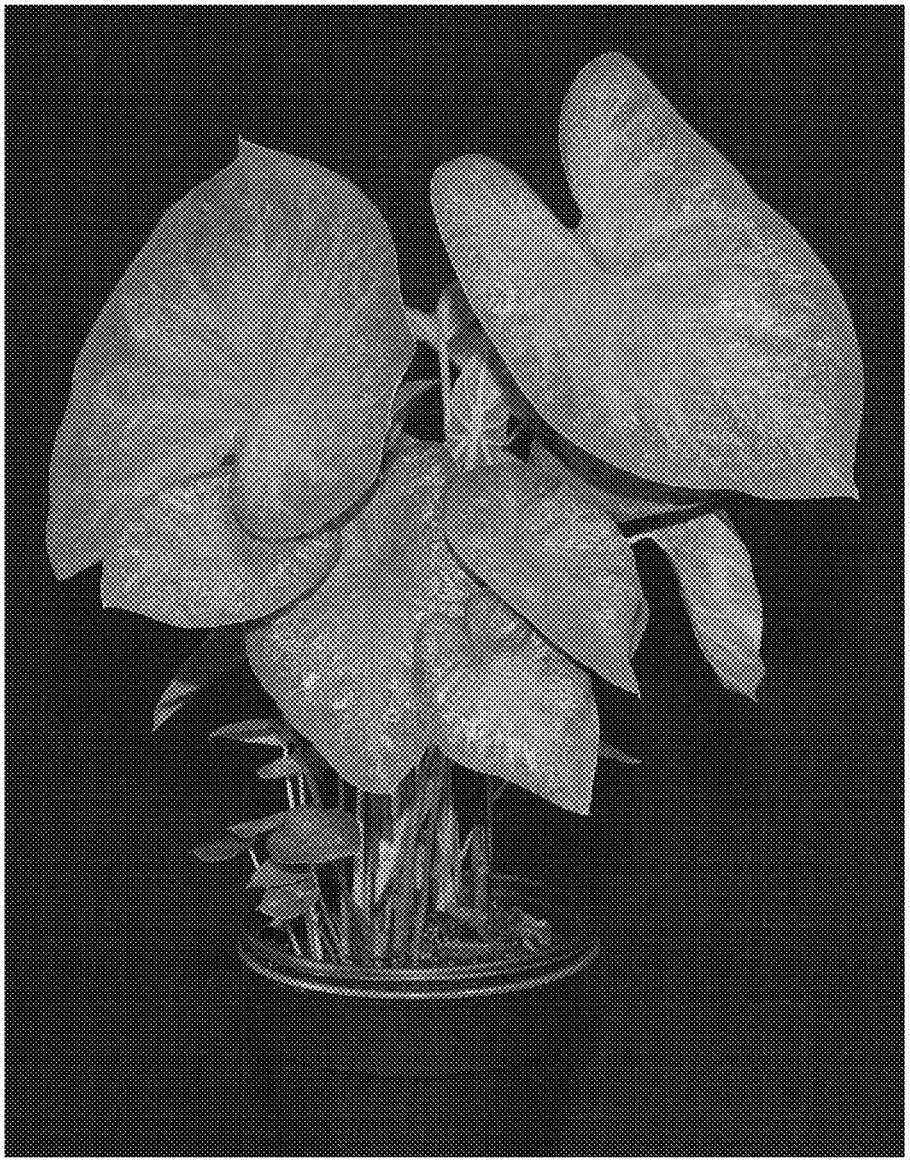

Botanical designation: *Caladium* X *hortulanum*.
Cultivar denomination: 'RSB OF15-200'.

BACKGROUND OF THE INVENTION

The present invention relates to a new and distinct cultivar of *Caladium* plant, botanically known as *Caladium* X *hortulanum*, commercially referred to as a fancy leaf-type *Caladium* and hereinafter referred to by the name 'RSB OF15-200'.

The objective of the Inventor's breeding program is to create new *Caladium* plants that have uniform plant habit, exceptional container and garden performance and attractive and unique leaf coloration.

The new *Caladium* plant originated from a cross-pollination made by the Inventor in April, 2014 in Avon Park, Florida of *Caladium* X *hortulanum* 'UF 4424', disclosed in U.S. Plant Pat. No. 25,598, as the female, or seed, parent with *Caladium* X *hortulanum* 'White Wonder', disclosed in U.S. Plant Pat. No. 21,044, as the male, or pollen, parent. The new *Caladium* plant was discovered and selected by the Inventor as a single plant within the progeny of the stated cross-pollination in a controlled outdoor nursery environment in Avon Park, Florida in September, 2015.

Asexual reproduction of the new *Caladium* plant by "chipping" the tubers (cutting the tuber into segments with each segment containing an axillary bud and tuber cortical tissue) in a controlled outdoor nursery environment in Zolfo Springs, Florida since April, 2016 has shown that the unique features of this new *Caladium* plant are stable and reproduced true to type in successive generations of asexual reproduction.

SUMMARY OF THE INVENTION

Plants of the new *Caladium* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'RSB OF15-200'. These characteristics in combination distinguish 'RSB OF15-200' as a new and distinct *Caladium* plant:

1. Upright plant habit and intermediate to tall in height; moderately dense, leafy and bushy appearance.
2. Moderately vigorous growth habit and rapid growth rate.
3. Fancy-type leaves with centers that have variable hues of reddish pink and surrounded by dark green-colored marginal areas, entire leaf with variable and random greenish white-colored speckles.
4. Petioles that are tannish green to tannish pink in color with greenish brown-colored stripes.

Plants of the new *Caladium* differ primarily from plants of the female parent, 'UF 4424', in the following characteristics:

1. Plants of the new *Caladium* are taller and more upright than plants of 'UF 4424'.
2. Leaves of plants of the new *Caladium* are fancy types whereas leaves of plants of 'UF 4424' are lance-types.
3. Leaves of plants of the new *Caladium* have centers with variable hues of reddish pink and surrounded by dark green-colored marginal areas whereas leaves of plants of 'UF 4424' are dark red in color with narrow green-colored and undulate margins.
4. Petioles of plants of the new *Caladium* are tannish green to tannish pink in color with greenish brown-colored stripes whereas petioles of plants of 'UF 4424' are reddish pink in color.

Plants of the new *Caladium* differ primarily from plants of the male parent, 'White Wonder', in the following characteristics:

1. Plants of the new *Caladium* are taller and more upright than plants of 'White Wonder.
2. Leaves of plants of the new *Caladium* are fancy types whereas leaves of plants of 'White Wonder' are lance types.
3. Leaves of plants of the new *Caladium* have centers with variable hues of reddish pink and surrounded by dark green-colored marginal areas whereas leaves of plants of 'White Wonder' are white to grey-green in color with light pink to white-colored venation and dark green-colored borders.

Plants of the new *Caladium* can be compared to plants of *Caladium* X *hortulanum* 'Rose Glow', disclosed in U.S. Plant Pat. No. 20,070. In side-by-side comparisons, plants of the new *Caladium* differ primarily from plants of 'Rose Glow' in the following characteristics:

1. Plants of the new *Caladium* are taller than plants of 'Rose Glow'.
2. Leaves of plants of the new *Caladium* have centers with variable hues of reddish pink and surrounded by dark green-colored marginal areas whereas leaves of plants of 'Rose Glow' are red purple in color with white-colored main veins, green-colored borders and dark green-colored margins.
3. Petioles of plants of the new *Caladium* are tannish green to tannish pink in color with greenish brown-colored stripes whereas petioles of plants of 'Rose Glow' are tannish green to tannish pink in color with greenish brown-colored stippling, streaks and tessellations without any stripes.

Plants of the new *Caladium* can also be compared to plants of *Caladium* X *hortulanum* 'Classic Pink', disclosed in U.S. Plant Pat. No. 27,093. In side-by-side comparisons, plants of the new *Caladium* differ primarily from plants of 'Classic Pink' in the following characteristics:

1. Plants of the new *Caladium* are taller than plants of 'Classic Pink'.
2. Plants of the new *Caladium* are not as freely clumping as plants of 'Classic Pink'.
3. Plants of the new *Caladium* have larger leaves than plants of 'Classic Pink'.
4. Leaves of plants of the new *Caladium* have centers with variable hues of reddish pink and surrounded by dark green-colored marginal areas whereas leaves of plants of 'Classic Pink' are deep rose pink in color surrounded by a narrow area of white-colored speckling and dark green-colored margins.
5. Petioles of plants of the new *Caladium* are tannish green to tannish pink in color with greenish brown-colored stripes whereas petioles of plants of 'Classic Pink' are reddish pink in color with bold darker-colored stripes.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet (FIG. 1) is a side perspective view of a typical plant of 'RSB OF15-200' grown in a container that has had its tuber de-eyed prior to planting.

Figure 2:
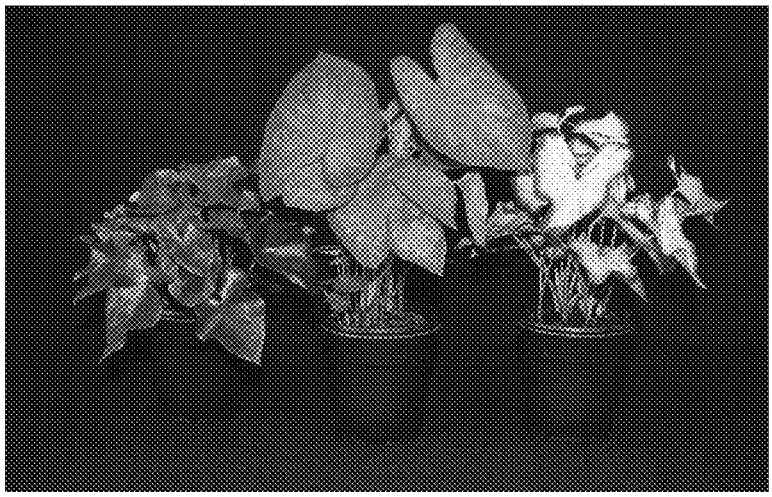

The photograph at the top of the second sheet (FIG. 2) is side perspective view of typical plants of the female parent, 'UF 4424' (left), 'RSB OF15-200' (center) and the male parent, 'White Wonder' (right).

Figure 3:
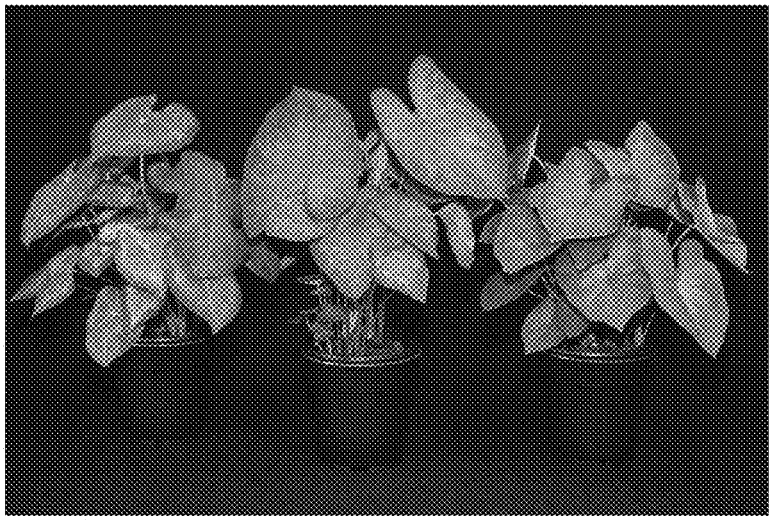

The photograph at the bottom of the second sheet (FIG. 3) is side perspective view of typical plants of 'Rose Glow' (left), 'RSB OF15-200' (center) and 'Classic Pink' (right).

Figure 4:
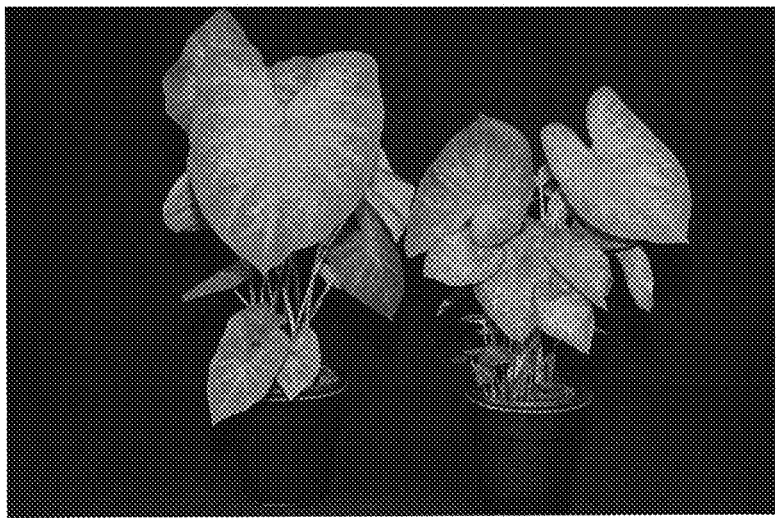

The photograph at the top of the third sheet (FIG. 4) is a comparison view of typical plants of 'RSB OF15-200' grown in containers, the plant on the left has not had its tuber de-eyed and the plant on the right has had its tuber de-eyed prior to planting.

Figure 5:
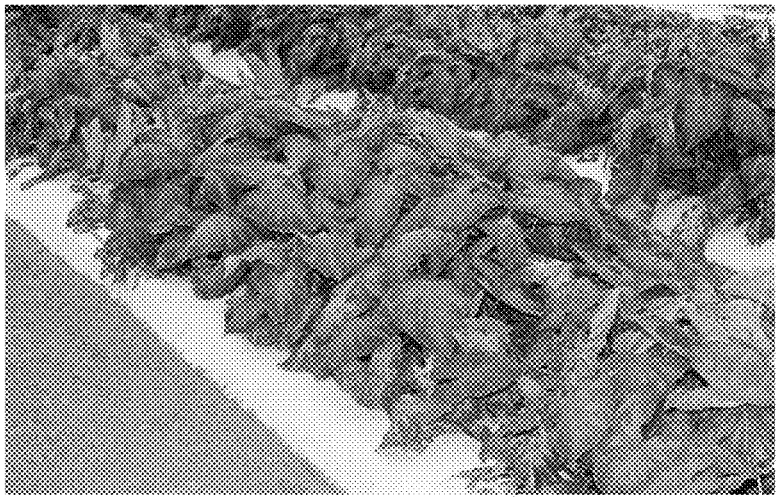

The photograph at the bottom of the third sheet (FIG. 5) is a side perspective view of typical plants of 'RSB OF15-200' grown in an open production field.

Figure 6:
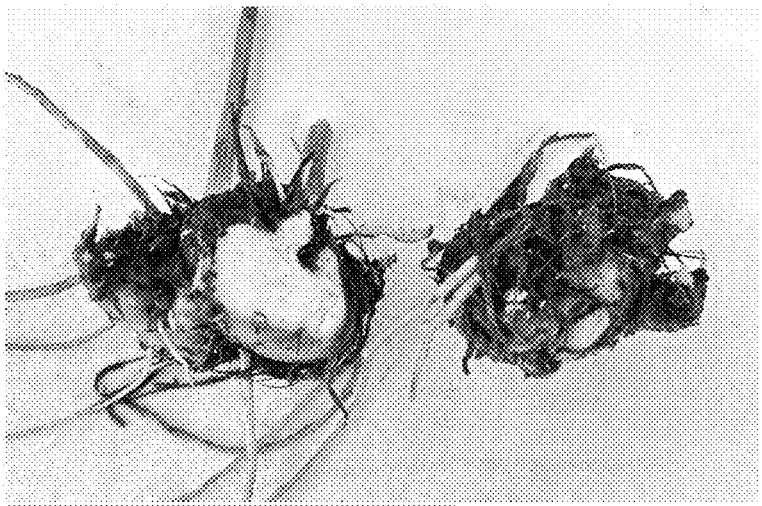

The photograph at the top of the fourth sheet (FIG. 6) is a close-up view of typical freshly-harvested tubers with roots and leaf petioles of 'RSB OF15-200'.

Figure 7:
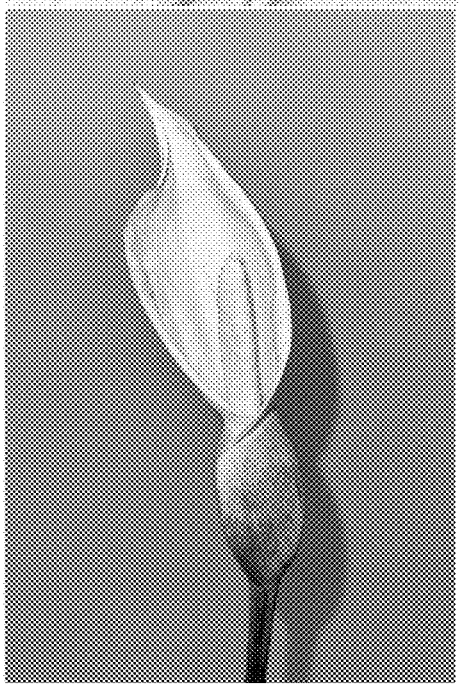

The photograph at the bottom of the fourth sheet (FIG. 7) is a close-up view of a typical inflorescence of 'RSB OF15-200'.

DETAILED BOTANICAL DESCRIPTION

The aforementioned photographs and following observations and measurements describe plants grown in 15-cm containers in a polypropylene-covered shade house (30% light reduction) in Avon Park, Florida and plants grown in ground beds under full sunlight conditions in an outdoor nursery in Crewsville, Florida. The plants were grown under cultural practices typical of commercial shade house and outdoor nursery production. During the production of the shade house-grown plants, day temperatures ranged from about 28° C. to 33° C., night temperatures ranged from about 22° C. to 25° C. and light levels were about 1,300 μmol. During the production of the outdoor nursery-grown plants, day temperatures ranged from about 29° C. to 35° C., night temperatures ranged from about 23° C. to 26° C. and full sunlight conditions. Plants grown in the shade house were eight weeks old and plants grown in the outdoor nursery were seven months old when the photographs and the detailed description were taken. In the following description, color references are made to The Royal Horticultural Society Colour Chart, 2001 and 2015 Editions, except where general terms of ordinary dictionary significance are used.

Botanical classification: *Caladium* X *hortulanum* 'RSB OF15-200'.

Parentage:

*Female, or seed, parent.*—*Caladium* X *hortulanum* 'UF 4424', disclosed in U.S. Plant Pat. No. 25,598.

*Male, or pollen, parent.*—*Caladium* X *hortulanum* 'White Wonder', disclosed in U.S. Plant Pat. No. 21,044.

Propagation:

*Type.*—By "chipping" the tubers.

*Time to initiate roots, summer.*—About seven to ten days at temperatures about 32° C.

*Time to initiate roots, winter.*—About two to three weeks at temperatures about 24° C.

*Tuber description* (*outdoor nursery-grown plants*).—Appearance: Multi-segmented and branched; individual segments are elliptic to ovate or irregular in shape. Height: About 3.7 cm to 3.9 cm. Diameter: About 4 cm to 7.8 cm. Segment height: About 1.3 cm to 2.1 cm. Segment diameter: About 1.5 cm to 1.7 cm. Axillary bud shape: Roughly triangular. Axillary bud height: About 2.5 mm to 3.5 mm. Axillary bud width: About 2.5 mm to 4 mm. Texture: Thick, starchy; somewhat brittle. Color: Periderm, freshly-harvested: Close to 199A to 199B. Periderm, dried: Close to 200A. Epidermis: Close to 158B to 158C. Cortical tissue: Close to 155B and 11D. Axillary buds: Close to 38B to 38C. Root description: Relatively thick, fleshy contractile roots with a few lateral branches; color, close to NN155D; actual color of the roots is dependent on substrate composition, water quality, fertilizer type and formulation, substrate temperature and physiological age of roots; root density, moderately dense.

Plant description:

*Plant type*.—Herbaceous perennial; suitable as a potted plant in containers 15-cm to 25-cm and suitable as a landscape plant in shaded and full sunlight areas.

*Plant and growth habit*.—Upright plant habit; intermediate to tall in height; moderately dense, leafy and bushy appearance; moderately vigorous growth habit and rapid growth rate; potted plants finish in saleable form in about six weeks after planting tubers; leaf petioles and leaves arise from one or more growing points on tubers; leaf petioles initially upright and leaning outwardly with development.

*Plant height, from soil level to top of foliar plane, shade house-grown potted plants*.—About 37 cm to 46 cm.

*Plant height, from soil level to top of floral plane, shade house-grown potted plants*.—About 43 cm.

*Plant diameter, shade house-grown potted plants*.—About 26 cm to 35 cm.

*Number of shoots per plant, shade house-grown potted plants, tubers de-eyed*.—About four to eight develop per #1 tuber.

*Number of shoots per plant, shade house-grown potted plants, tubers not de-eyed*.—About two to three develop per #1 tuber.

*Cataphylls, shade house-grown potted plants*.—Length: About 5.9 cm to 9 cm. Width: About 1.2 cm to 1.6 cm. Shape: Strap to wedge-shaped. Apex: Acute, cuspidate or emarginate. Base: Sheathing the stem. Texture, outer and inner surfaces: Smooth, glabrous. Color, outer and inner surfaces: Close to 200A to 200B.

Leaf description:

*Arrangement and type*.—Alternate; simple; fancy-type.

*Length, shade house-grown potted plants*.—About 17 cm to 29 cm.

*Width, shade house-grown potted plants*.—About 14 cm to 20.4 cm.

*Shape*.—Broadly ovate with cordate tendencies.

*Apex*.—Acuminate to acute.

*Base*.—Sagittate to peltate, cordate.

*Margin*.—Entire; mostly flat with broad undulations.

*Texture and luster, upper surface*.—Smooth, glabrous; dull sheen.

*Texture and luster, lower surface*.—Smooth, glabrous; slightly glaucous; dull sheen.

*Venation pattern*.—Pinnate and palmate.

*Color, shade house-grown potted plants*.—When developing and fully expanded leaves, upper surface: Centers: Close to 185B, 185C, 49D, 191A and/or 191A tinged with close to 187A with variable blotches, flecks and speckles, close to N155C and N155D. Marginal areas: Close to 191A tinged with close to 189A or 187A with variable blotches, flecks and speckles, close to N155C to N155D; edges, close to 187A. Basal notch: Close to 187B. Main vein: Close to 181D streaked with close to 184B. Lateral venation: Close to 182C and 185D; smaller veins, tinged with close to 187A. When developing and fully expanded leaves, lower surface: Centers: Close to 51A, 51B, 51C and/or 56A variably blotched and flushed with close to 183A to 183B with variable blotches, flecks and speckles, close to N155B and 155C. Marginal areas: Close to NN137A with variable blotches, flecks and speckles, close to 155C; edges, close to 187A to 187B. Basal notch: Close to 187A. Midvein and lateral venation: Close to 51A and 51A to 51B.

*Petioles*.—Aspect: Initially upright and straight and leaning outwardly with development; flexible. Length, shade house-grown potted plants: About 26.5 cm to 37 cm. Diameter, distally, shade house-grown potted plants: About 2.5 mm to 3 mm. Diameter, proximally, shade house-grown potted plants: About 6 mm to 10 mm. Texture: Smooth, glabrous; distally, glaucous and proximally, glossy. Color, shade house-grown potted plants: Close to 161D, 181D and/or 56D with streaks, stippling and stripes, close to N200A; may be flushed with close to 199C to 199D; just below the leaf junction, close to 56C variably streaked with close to 184C and 182A. Wing length, shade house-grown potted plants: About 6 cm to 11 cm. Wing diameter, shade house-grown potted plants: About 7 mm to 10 mm. Texture and luster, inner and outer surfaces: Smooth, glabrous; dull to slightly glossy. Wing color, shade house-grown potted plants: Outer surface: Close to 56D variably stippled and streaked with close to N200A and tinged with close to 147A. Inner surface: Close to N155C; colors and patterns from the outer surface are visible on the inner surface.

Inflorescence description:

*Inflorescence arrangement*.—Upright hooded spathes surrounding a columnar spadix borne on an upright scape; spadix with sessile, simple female and male flowers separated into two zones; female flowers develop on the proximal one-third of the spadix; male flowers develop on the distal two-thirds of the spadix; sterile flowers develop at junction of female and male flower zones; near this junction, the spathe constricts and surrounds and encloses the female flowers; spathe open and cupped around male flowers.

*Fragrance*.—Night-fragrant; jasmine-like with camphor note.

*Natural flowering season and flower longevity*.—Plants of the new *Caladium* typically flower during the spring and summer in central Florida; flowers develop about five months after growth commences; inflorescences last about three days before fading; inflorescences persistent.

*Spathe*.—Length, overall: About 16 cm. Length, distal open portion: About 10.4 cm. Length, proximal closed portion: About 5.6 cm. Width, distal open portion: About 4 cm. Depth, distal open portion: About 2.6 cm. Width, at constriction: About 1.5 cm to 2.3 cm. Width, proximal closed portion: About 2.7 cm to 3.1 cm. Shape, open portion: Elliptic to slightly obovate. Apex: Acute. Base: Acute. Margin: Entire; reflexed. Texture and luster, front surface: Smooth, glabrous; dull sheen. Texture and luster, rear surface: Smooth, glabrous; slightly glaucous; dull sheen. Color, front surface: Distal open portion: Close to N155C to N155D; with subsequent development, distally becoming closer to 199B and 200C. Proximal closed portion: Close to 148D, distally, close to 194C to 194D and flushed with close to 187A; color does not change with subsequent development. Color, rear surface: Distal open portion: Close to 155A to 155B; central area, close to 145D; color does not change with subsequent development. Proximal closed portion: Close to 147C to 147D, 145C and 146D with random flecks and streaks, close to 183C to 183D; color does not change with subsequent development.

*Spadix*.—Length, overall: About 9.6 cm. Length, male flower zone: About 7.7 cm. Length, sterile zone: About 1.9 cm. Length, female flower zone: About 1.9 cm. Diameter, male flower zone: About 1 cm. Diameter, sterile flower zone: About 6 mm. Diameter, female flower zone: About 9 mm. Shape: Columnar, spindle-shaped. Apex: Acute to obtuse, rounded. Base: Obtuse. Aspect: Upright. Color, mature, male zone: Close to 159D. Color, mature, sterile zone: Close to 159D. Color, mature, female zone: Stigmas, close to 9C to 9D; ovaries, close to 159B to 159C. Male flowers: Quantity per spadix: About 294. Shape: Obovate. Height: About 2 mm. Diameter: About 3 mm to 4.5 mm. Pollen amount: Moderate. Pollen color: Close to 8B to 8C. Female flowers: Quantity per spadix: About 154. Shape: Obovate. Height: About 1.5 mm. Diameter: About 3 mm. Stigma color: Close to 9C to 9D. Ovary color: Close to 159B to 159C.

*Scapes*.—Length: About 27 cm. Diameter: About 7 mm to 8 mm. Strength: Sturdy; flexible. Aspect: Mostly erect, straight. Texture and luster: Smooth, glabrous; glaucous and slightly glossy. Color: Close to 200C to 200D with stripes, close to 199D tinged with close to 148B to 148C; just below spathe, close to 147B to 147C striped with close to 200C.

*Seeds and fruits*.—To date, seed and fruit development have not been observed on plants of the new *Caladium*.

Pathogen tolerance/resistance: Plants of the new *Caladium* have been observed to have average tolerance to *Pythium* Root Rot and average tolerance to *Xanthomonas* Leaf Spot. Plants of the new *Caladium* have not been observed to have tolerance/resistance to other pathogens common to *Caladium* plants.

Temperature tolerance: Plants of the new *Caladium* have been observed to tolerate temperatures ranging from about 7° C. to about 40° C. and are suitable for USDA Hardiness Zones 8A to 11. In cooler zones, tubers can be "lifted" prior to first freeze and stored in a cool dry environment to overwinter for re-planting the following spring.

It is claimed:

1. A new and distinct *Caladium* plant named 'RSB OF15-200' as herein illustrated and described herein.

* * * * *